United States Patent [19]

Löliger et al.

[11] Patent Number: 5,427,814
[45] Date of Patent: Jun. 27, 1995

[54] PROCESS FOR PROTECTING A FAT AGAINST OXIDATION

[75] Inventors: Jürg Löliger, Corseaux; Francoise Saucy, Blonay, both of Switzerland

[73] Assignee: Nestec S.A., Vevey, Switzerland

[21] Appl. No.: 202,892

[22] Filed: Feb. 28, 1994

Related U.S. Application Data

[60] Division of Ser. No. 785,496, Oct. 31, 1991, Pat. No. 5,364,886, which is a continuation of Ser. No. 297,120, Jan. 13, 1989, abandoned.

[30] Foreign Application Priority Data

Feb. 3, 1988 [CH] Switzerland ............... 374/88

[51] Int. Cl.$^6$ .............. A61K 7/40; A61K 47/00; A23D 9/06
[52] U.S. Cl. .............. 426/610; 252/397; 514/221; 514/772; 554/2; 554/3; 554/4
[58] Field of Search ............. 260/398.5; 514/221, 514/772; 426/601, 610; 252/397

[56] References Cited

U.S. PATENT DOCUMENTS

| | | | |
|---|---|---|---|
| 2,324,348 | 7/1943 | Anderson | 252/367 |
| 2,333,655 | 11/1943 | Mattill et al. | 99/163 |
| 2,333,656 | 11/1943 | Mattill et al. | 99/163 |
| 2,377,029 | 5/1945 | Norris | 99/163 |
| 2,383,815 | 8/1945 | Riemschneider et al. | 260/398.5 |
| 2,383,816 | 8/1945 | Riemschneider et al. | 260/398.5 |
| 2,432,698 | 12/1947 | Taub et al. | 514/274 |
| 2,433,593 | 12/1947 | Buxton | 260/398.5 |
| 2,493,288 | 1/1950 | Hall | 260/398.5 |
| 2,511,427 | 6/1950 | Buxton et al. | 514/274 |
| 3,294,825 | 12/1966 | Pottier | 260/398.5 |
| 4,009,271 | 2/1977 | von Bebenburg et al. | 514/221 |
| 4,765,927 | 8/1988 | Nomura et al. | 260/398.5 |
| 5,077,069 | 12/1991 | Chang | 426/330.6 |
| 5,084,289 | 1/1992 | Shin | 426/330.6 |

FOREIGN PATENT DOCUMENTS 5809041 10/1985 European Pat. Off.

OTHER PUBLICATIONS

Schultz, ed. *Symposium on Foods: Lipids and Their Oxidation*, AVI Publishing Co., Inc. Conneticut, 1962, pp. 178–189.

Translation of Ito, et al. Japanese Patent Kokai No. 55–69688 (1980).

Lea, "Some Nutritional and Allied Problems Confronting the Food Manufacturer: Technological Aspects of Antioxidants", J. Sci. Food Agric., 9, Oct., 1958. pp. 621–632.

Evans, Chemical Abstracts, CA: 6653C "Tocopherol Oxidation in Fats. Hydrogenated Soybean Oil", (1959).

Pongracz, "Antioxidant Mixtures for Use in Food." Ianternat. J. Vit. Nutr. Res. 43 (1973): 517–525.

*Primary Examiner*—C. Warren Ivy
*Assistant Examiner*—D. Margaret M. Mach
*Attorney, Agent, or Firm*—Vogt & O'Donnell

[57] ABSTRACT

A fat is protected from oxidation by, in one process embodiment, forming a mixture of tocopherol and lecithin at a temperature not greater than 60° C., mixing ascorbic acid dissolved in a polar solvent into the tocopherol and lecithin mixture, eliminating the solvent from the mixture at a temperature not greater than 60° C. and then, incorporating the mixture into a fat. In another embodiment, lecithin is added to a fat, and tocopherol and ascorbic acid dissolved in a polar solvent are added to the lecithin-added fat after which, the solvent is eliminated from the fat.

11 Claims, No Drawings

PROCESS FOR PROTECTING A FAT AGAINST OXIDATION

CROSS REFERENCE TO RELATED APPLICATIONS

This is a divisional application of application Ser. No. 07/785,496, now U.S. Pat. No. 5,364,886, filed Oct. 31, 1991, which, in turn, is a continuation application of application Ser. No. 07/297,120 filed Jan. 13, 1989, now abandoned.

BACKGROUND OF THE INVENTION

This invention relates to a synergic antioxidant mixture intended to protect lipids against oxidation. The current trend in the field of antioxidants, particularly for use in foods, is to give preference to natural compounds showing antioxidant activity.

Esters of ascorbic acid with saturated fatty acids, particularly ascorbyl palmitate (AP) and ascorbyl stearate (AS), are known as antioxidants for lipids. This is also the case with tocopherols (TL) which have been found to show antioxidant activity in animal fats in which they are not naturally present. It is also known that a mixture of AP and TL is more active than each of these compounds on its own.

It has also been shown, for example by G. Pongraz in In.J.Vit.Nutr.Res. 43 (1973), that lecithin (LC), although not having any antioxidant activity of its own, greatly increases the activity of mixtures of AP and TL in butter oil and in sunflower seed oil.

This observation is confirmed in published Japanese patent application no. 80.069688 which relates to a mixture of AS, TL and LC in safflower oil and in lard.

In these known mixtures, the ascorbic acid (AA) is not used as such, but in ester form (AP, AS) for the simple reason that it is not liposoluble. According to G. Pongraz in the Article cited above, AP and AS are equivalent from the point of view of their antioxidant activity in lipids, preference being attributed to AP by virtue of its slightly better liposolubility.

SUMMARY OF THE INVENTION

It has now surprisingly been found that, when used in the presence of TL and LC, AA shows far better antioxidant activity than its esters in anhydrous systems, particularly lipids.

Thus, the synergic antioxidant mixture according to the invention is characterized in that it comprises tocopherol, ascorbic acid and a natural emulsifier.

The present invention also relates to a process for the protection of a fat or a fat-containing food or cosmetic product against oxidation, characterized in that effective quantities of tocopherol, ascorbic acid and natural emulsifier are incorporated in the fat or in the food or cosmetic product and relates to processes for preparing the antioxidant mixture and incorporating it into a fat.

DETAILED DESCRIPTION OF THE INVENTIONS

The tocopherol used may be α-tocopherol, β-tocopherol, γ-tocopherol, δ-tocopherol or mixtures thereof, for example a natural mixture emanating from a vegetable oil, for example soybean oil, wheatgerm oil, or cottonseed oil.

In the context of the invention, "natural emulsifiers" are understood to be naturally occurring nonionic surfactants, for example saponins, or ionic surfactants, for example phospholipids, of animal or vegetable origin, of milk, egg, or soybean, preferably lecithins, for example commercial lecithins, purified lecithins, soya lecithin and egg yolk lecithin and fractions thereof. The type of emulsifier used has only a secondary bearing on the effect observed providing it is capable of forming a stable dispersion of the AA in an anhydrous product, for example a fat or a food containing a fat or even a cosmetic product containing a fat. It is preferred to use soya lecithins or fractions thereof which are abundantly available and economical.

The antioxidant mixture according to the invention advantageously contains from 2.5 to 10% and, preferably, approximately 5% TL and from 2.5 to 20% and, preferably, from 5 to 20% AA, based on the weight of the natural emulsifier.

The present invention also relates to a process for the protection of a fat or a fat-containing food or cosmetic product against oxidation, characterized in that effective quantities of tocopherol, ascorbic acid and natural emulsifier are incorporated in the fat or in the food or cosmetic product.

In the process according to the invention, the antioxidant mixture is preferably used in a quantity of 0.55 to 2.3% by weight, based on the fat. If less than 0.55% by weight is used, there is a danger that the desired synergic effect might not be obtained on account of the inadequate quantity of emulsifier or antioxidant. If more than 2.3% by weight is used, there is a danger that unwanted secondary effects, such as for example variations in taste or odour or foaming, might occur.

The mixture may of course be used as such or, alternatively, the various constituents of the mixture may be separately incorporated in the fat to be protected. In cases where, for example, the fat is a vegetable oil already naturally containing TL, for example corn oil, it is sufficient to add the AA and the emulsifier. The same also applies, for example, in the case of a soybean oil which would naturally contain lecithin, in which case the TL and the AA would be added thereto.

In one advantageous embodiment, the mixture is prepared by initially introducing LC and TC with stirring at a temperature below or equal to 60° C., preferably while an inert gas, for example nitrogen, is bubbled through. The AA dissolved in a polar solvent, preferably of low boiling point, for example ethanol, is then progressively added to the resulting premix, after which the solvent is eliminated at a temperature of ≦60° C., for example under a light vacuum. The mixture obtained is in the form of a transparent and viscous liquid. This mixture may be used in different ways, for example by incorporation in a fat to be protected, preferably at elevated temperature, the mixture being at approximately 60° C., with vigorous stirring.

In another advantageous embodiment, the AA and, optionally, the TL are incorporated in the fat to which the lecithin was added beforehand, preferably in the form of a solution in a polar solvent, for example in ethyl alcohol, after which the solvent is removed. The fats to be protected in accordance with the invention are preferably those which are most vulnerable to oxidation, for example those which are rich in unsaturated fatty acids, particularly polyunsaturated fatty acids. Fats such as these include vegetable oils, for example wheatgerm oil, grapeseed oil, corn oil, soybean oil, safflower oil, olive oil, evening primose oil, borage oil, or particularly black currant seed oil. Examples of animal fats vulnerable to oxidation are chicken fat, butter oil, or oils of marine animals, particularly fish.

The foods and cosmetic products to be protected are preferably those which contain fats such as these.

EXAMPLES

The invention is illustrated by the following Examples in which the percentages and parts are by weight unless otherwise indicated.

EXAMPLES 1 TO 6

The antioxidant power of the mixtures according to the invention in the protection of fish oil against oxidation is evaluated by the FIRA.ASTELL ® accelerated oxidation test.

Preparation of the samples

Samples of 4 g stabilized oil are prepared as follows: The antioxidants are dissolved in absolute ethanol in a quantity of 125 mg/25 ml and the solution is mixed with the oil to which the lecithin has optionally been added. The ethanol is used in a quantity of 0.5 to 1.5 ml, depending on the concentrations used. The ethanol is then eliminated by evaporation at 60° C. for 2 hours while the sample is purged with nitrogen.

Oxidation test

The sample is placed in a hermetically sealed glass reactor provided with a magnetic stirrer. The reactor itself is placed in an oil bath at the selected temperature. The atmosphere in the reactor is air. The head space communicates by a flexible tube with a differential manometer connected to a recorder. When oxidation is in progress, the quantity of oxygen absorbed is indicated by the pressure difference observed. The induction time is graphically determined from the transcribed pressure curve as a function of time by intersection of the tangent to the curve with the time axis.

The results obtained are shown in Table I below, in which the induction times obtained without additive (C0), by the various additives on their own (C1 to C3) or in pairs (C4 to C13) are shown by way of comparison.

TABLE I

| | Antioxidant additive, based on oil | | | Induction time[1] (h) at | | |
|---|---|---|---|---|---|---|
| | TL (ppm) | AA(ppm) | LC(%) | 60° C. | 80° C. | 100° C. |
| Examples | | | | | | |
| 1 | 250 | 250 | 1 | — | 2.7 | — |
| 2 | 250 | 500 | 1 | — | 9.1 | — |
| 3 | 500 | 500 | 1 | — | 12.8 | 3 |
| 4 | 500 | 1000 | 1 | — | 23.2 | 5.2 |
| 5 | 1000 | 500 | 1 | — | 11.2 | — |
| 6 | 500 | 2000 | 1 | — | 18 | — |
| Comparisons: | | | | | | |
| C0 | — | — | — | 7 | 0.5 | 0.1 |
| C1 | 500 | — | — | 12 | — | — |
| C2 | — | 1000 | — | 11.5 | — | — |
| C3 | — | — | 1 | 10 | 1.6 | — |
| C4 | 500 | 250 | — | 11.7 | — | — |
| C5 | 500 | 500 | — | 17 | 2.9 | — |
| C6 | 250 | 500 | — | — | 2.5 | — |
| C7 | 250 | 1000 | — | — | 2.9 | — |
| C8 | 500 | 1000 | — | — | 2.5 | — |
| C9 | 1000 | 500 | — | — | 3.6 | — |
| C10 | 2000 | 2000 | — | — | 2.7 | — |
| C11 | 500 | — | 1 | — | — | 2.2 |
| C12 | 1000 | — | 1 | — | 1.2 | — |

TABLE I-continued

| | Antioxidant additive, based on oil | | | Induction time[1] (h) at | | |
|---|---|---|---|---|---|---|
| | TL (ppm) | AA(ppm) | LC(%) | 60° C. | 80° C. | 100° C. |
| C13 | — | 500 | 1 | — | — | 1.1 |

Legend:
ppm = parts per million
LC = purified soya lecithin (TOPCITHIN ®).
[1]The results obtained for the induction time at the various temperatures indicated may be compared by using an approximate factor of 4 for the values at 100° C. in relation to the values at 80° C.

Table I above shows that the addition of the ternary mixture TL, AA and LC has an effect such that the fish oil remains stable approximately 5 to 26 times longer than the additive-free oil (1 and 4 compared with C0) and approximately 12 times longer than the oil containing one or other of the antioxidants in comparable quantities (4 compared with C1–C3).

The antioxidant effect of the ternary mixture is also higher by a factor of approximately 3 to 9 than that of the binary mixtures (2 to 5 compared with C5, C6, C8 and C9).

Accordingly, the various additives have a synergic effect.

EXAMPLE 7

The induction times of fish oil containing the ternary mixtures of Examples 3 and 4 are compared with those obtained for ascorbyl palmitate (AP) on its own or in the form of binary or ternary mixtures with TL and LC using the FIRA.ASTELL ® oxidation test described above.

The results are shown in Table II below.

TABLE II

| Comparison | Antioxidant additive | | | Induction time (h) at | | |
|---|---|---|---|---|---|---|
| | TL(ppm) | LC(%) | AA[1](ppm) | 60° C. | 80° C. | 100° C. |
| C14 | — | — | 500 | 8.1 | 1.8 | — |
| C15 | — | 1 | 500 | — | — | 0.2 |
| C16 | — | 1 | 1000 | — | — | 1.3 |
| C17 | 500 | 1 | 500 | — | 4.1 | 1 |
| C18 | 500 | 1 | 1000 | — | 8.1 | 2.2 |
| According to Example 3 | | | | — | 12.8 | 3 |
| According to Example 4 | | | | — | 23.2 | 5.2 |

Legend:
[1]The content indicated is based on ascorbic acid in the form of ascorbyl palmitate.
LC = TOPCITHIN ®

Comparison of the induction times of the ternary systems C17 and Example 3 and C18 and Example 4, respectively, shows that the antioxidant effect is increased by a factor of 2.3 to 3.1 by replacement of the ascorbyl palmitate by ascorbic acid. This is all the more unexpected as ascorbic acid is completely insoluble in the oils.

EXAMPLES 8 TO 12

The induction times at 100° C. of fish oil stabilized by antioxidant mixtures containing 500 ppm TL, 1000 ppm AA and 1% of various lecithins are determined by the Fira.Astell ® oxidation test described above. The results are shown in Table III below:

TABLE III

| Example | Emulsifier | Induction time (h) |
|---|---|---|
| 8 | AZOL ®: soya lecithin fraction mixed with approxiately 60% triglycerides | 6 |
| 9 | CENTROPHASE ®: a mixture of substantially equal quantities | 2.7 |

TABLE III-continued

| Example | Emulsifier | Induction time (h) |
|---|---|---|
| | of soya lecithin and triglycerides | |
| 10 | M-C-THIN ®: a mixture of soya phospholipides: phosphatidyl choline, phosphatidyl ethanolamine, meso-inositol phosphatide | 4.2 |
| 11 | METHARIN ®: a mixture of soya phospholipides and mono-, di- and triglycerides | 1.5 |
| 12 | TOPCITHIN ®: refined soya lecithin poor in heavy metals | 5.2 |

EXAMPLE 13

The induction times of chicken fat stabilized with the antioxidant additives is determined using the RANCIMAT ® accelerated oxidation test.

The Rancimat test differs from the FIRA.ASTELL ® test in the fact that air is passed through a test tube containing a 5 g sample of fat at 100° C. and the conductivity of the volatile secondary products formed during oxidation and entrained with the stream of air is measured. The induction time is graphically determined from the recorded conductivity curve as a function of time by intersection of the tangent to the curve with the time axis.

The results are shown in Table IV below:

TABLE IV

| | Antioxidant additive | | | Induction time (h) |
|---|---|---|---|---|
| | TL(ppm) | AA(ppm) | LC(%) | |
| | 1000 | 500 | 1 | 47.9 |
| Comparison | 1000 | — | — | 13 |
| Comparison | — | 500 | — | 7.4 |
| Without additive | | | | 5 |

Legend:
LC = TOPCITHIN ®

The surprising antioxidant effect of the ternary mixture is confirmed in chicken fat.

EXAMPLE 14

The induction times at 100° C. of corn oil stabilized with various antioxidant additives is determined using the RANCIMAT ® oxidation test described above. Corn oil already naturally contains approximately 310 ppm δ-tocopherol (TL).

The results are shown in Table V below:

TABLE V

| | Antioxidant additive | | Induction time (h) |
|---|---|---|---|
| | AA(ppm) | LC(%) | |
| | 250 | 0.5 | 34.6 |
| Comparison | 250 | — | 20.8 |
| With no antioxidant other than the TL naturally present | | | 10 |

Legend:
LC = TOPCITHIN ®

It can be seen that the surprising antioxidant effect of the ternary mixture is confirmed in the case of corn oil where one of the antioxidants of the mixture, namely tocopherol, is already naturally present.

EXAMPLES 15 TO 17

(Example 15)

100 g LC (TOPCITHIN ®) and 60 g TL are heated to 60° C. while nitrogen is bubbled through. 100 g AA dissolved in 2.5 l absolute ethanol are then progressively added thereto with mechanical stirring over a period of 5 h. The ethanol is then evaporated at 60° C. under a light vacuum until the mixture is constant in weight. On completion of the operation, the mixture becomes completely transparent.

99 kg black currant seed oil are heated under nitrogen to 90° C. in a closed double-jacketed tank. The above antioxidant mixture heated to 60° C. is then added with vigorous stirring, after which the stabilized oil is cooled to ambient temperature over a period of 20 minutes.

(Examples 15 to 17)

The induction times at 100° C. of the oil stabilized with different quantities of antioxidant additives and without additive is determined by the FIRA.ASTELL ® oxidation test described above.

The results are shown in Table VI below:

TABLE VI

| | Antioxidant additive | | | Induction time (h) |
|---|---|---|---|---|
| | LC(%) | TC(ppm) | AA(ppm) | |
| Example | | | | |
| 15 | 1 | 600 | 1000 | 23 |
| 16 | 0.5 | 250 | 500 | 14.2 |
| 17 | 2 | 1000 | 2000 | 30 |
| Comparison | | no additive | | 3.5 |

The non-stabilized black currant seed oil has an induction time approximately 4 to 9 times shorter than those obtained by addition of the antioxidant mixtures LC, TL and AA.

We claim:

1. A process for protection of a fat against oxidation comprising stirring tocopherol and a lecithin at a temperature not greater than 60° C. to form a mixture, dissolving ascorbic acid in a polar solvent to form a solution, mixing the dissolved ascorbic acid solution into the tocopherol and lecithin mixture, eliminating the solvent from the tocopherol, lecithin and ascorbic acid solution mixture at a temperature not greater than 60° C. and then incorporating the mixture into a fat.

2. A process according to claim 1 wherein an inert gas is bubbled through the tocopherol and lecithin while stirring the tocopherol and lecithin.

3. A process according to claim 1 wherein the polar solvent is ethanol.

4. A process according to claim 1 wherein the tocopherol is in an amount of from 2.5% to 10% by weight based upon a weight of the lecithin and the ascorbic acid is in an amount of from 2.5% to 20% by weight based upon a weight of the lecithin, and the tocopherol, ascorbic acid and lecithin are incorporated in the fat in an amount of from 0.55% to 2.3% by weight based upon a weight of the fat.

5. A process according to claim 1 wherein the fat is contained in a cosmetic product.

6. A process according to claim 1 wherein the fat is contained in a food product.

7. A process for protection of a fat against oxidation comprising adding a lecithin to a fat, dissolving tocopherol and ascorbic acid in a polar solvent to form a solution, adding the tocopherol and ascorbic acid solution to the lecithin-added fat and then eliminating the solvent from the fat.

8. A process according to claim 7 wherein the polar solvent is ethanol.

9. A process according to claim 7 wherein the tocopherol is in an amount of from 2.5% to 10% by weight based upon a weight of the lecithin and the ascorbic acid is in an amount of from 2.5% to 20% by weight based upon a weight of the lecithin, and the tocopherol, ascorbic acid and lecithin are incorporated in the fat in an amount of from 0.55% to 2.3% by weight based upon a weight of the fat.

10. A process according to claim 7 wherein the fat is contained in a cosmetic product.

11. A process according to claim 7 wherein the fat is contained in a food product.

* * * * *